United States Patent
Ruhl et al.

(10) Patent No.: US 10,024,831 B2
(45) Date of Patent: Jul. 17, 2018

(54) GRAPHENE GAS SENSOR FOR MEASURING THE CONCENTRATION OF CARBON DIOXIDE IN GAS ENVIRONMENTS

(71) Applicant: Infineon Technologies AG, Neubiberg (DE)

(72) Inventors: Guenther Ruhl, Regensburg (DE); Thomas Hirsch, Regensburg (DE); Alexander Zoepfl, Regensburg (DE)

(73) Assignee: Infineon Technologies AG, Neubiberg (DE)

( * ) Notice: Subject to any disclaimer, the term of this patent is extended or adjusted under 35 U.S.C. 154(b) by 188 days.

(21) Appl. No.: 14/751,660

(22) Filed: Jun. 26, 2015

(65) Prior Publication Data

US 2015/0377824 A1    Dec. 31, 2015

(30) Foreign Application Priority Data

Jun. 26, 2014   (DE) .......................... 10 2014 212 282

(51) Int. Cl.
  *G01N 33/00* (2006.01)
  *G01N 27/12* (2006.01)

(52) U.S. Cl.
  CPC ......... *G01N 33/004* (2013.01); *G01N 27/127* (2013.01)

(58) Field of Classification Search
  CPC .......... G01N 33/0031–33/0059; G01N 27/127
  See application file for complete search history.

(56) References Cited

U.S. PATENT DOCUMENTS

| 2005/0097941 A1* | 5/2005 | Sandvik | G01N 27/4141 73/31.06 |
|---|---|---|---|
| 2011/0057168 A1* | 3/2011 | Kobayashi | B82Y 10/00 257/24 |
| 2012/0171775 A1* | 7/2012 | Vogt | B82Y 15/00 436/151 |
| 2012/0186987 A1* | 7/2012 | Mirsky | G01N 27/126 205/334 |

(Continued)

FOREIGN PATENT DOCUMENTS

JP    2002328108 A    * 11/2002

OTHER PUBLICATIONS

Ying Yang, Chungui Tian, Jingchao Wang, Li Sun, Keying Shi, Wei Zhou, and Honggang Fu, Facile synthesis of novel 3D nanoflower-like CuxO/multilayer graphene composites for room temperature NOx gas sensor application, Nanoscale, 6 (2014) 7369-7378.*

(Continued)

*Primary Examiner* — Susan D Leong
*Assistant Examiner* — Joshua L Allen
(74) *Attorney, Agent, or Firm* — Eschweiler & Potashnik, LLC

(57) ABSTRACT

A gas sensor for measuring a concentration of carbon dioxide in a gas environment (GE) is provided. The gas sensor includes a graphene layer having a side facing towards the gas environment (GE), an electrode layer including a plurality of electrodes electrically connected to the graphene layer, and a chalcogenide layer covering at least a part of the side of the graphene layer facing towards the gas environment (GE).

14 Claims, 4 Drawing Sheets

(56) References Cited

U.S. PATENT DOCUMENTS

| | | | | |
|---|---|---|---|---|
| 2013/0056703 A1* | 3/2013 | Elian | .................... | G01N 27/127 |
| | | | | 257/9 |
| 2013/0270534 A1* | 10/2013 | Hwang | ............... | H01L 51/0533 |
| | | | | 257/40 |
| 2014/0196522 A1* | 7/2014 | Borini | ...................... | G01N 7/00 |
| | | | | 73/29.03 |
| 2014/0247529 A1* | 9/2014 | Borini | .................... | H02H 5/083 |
| | | | | 361/91.2 |
| 2014/0260545 A1 | 9/2014 | Ruhl et al. | | |

OTHER PUBLICATIONS

Paul L. Kebabian and Andrew Freedman, Fluoropolymer-based capacitive carbon dioxide sensor, Meas. Sci. Technol. 17 (2006) 703-710.*

Ming Yang, Ying Hou, Nicholas A. Kotov, Graphene-baed multilayers: Critical evaluation of materials assembly techniques, Nano Today, 7 (2012) 430-447.*

Ueki et al. (JP 2002328108 A, machine translation).*

Yang, et al. "Facile synthesis of novel 3D nanoflower-like CuxO/multilayer graphene composites for room temperature NOx gas sensor application.", Nanoscale, 2014, 6, 7369-7378.

* cited by examiner

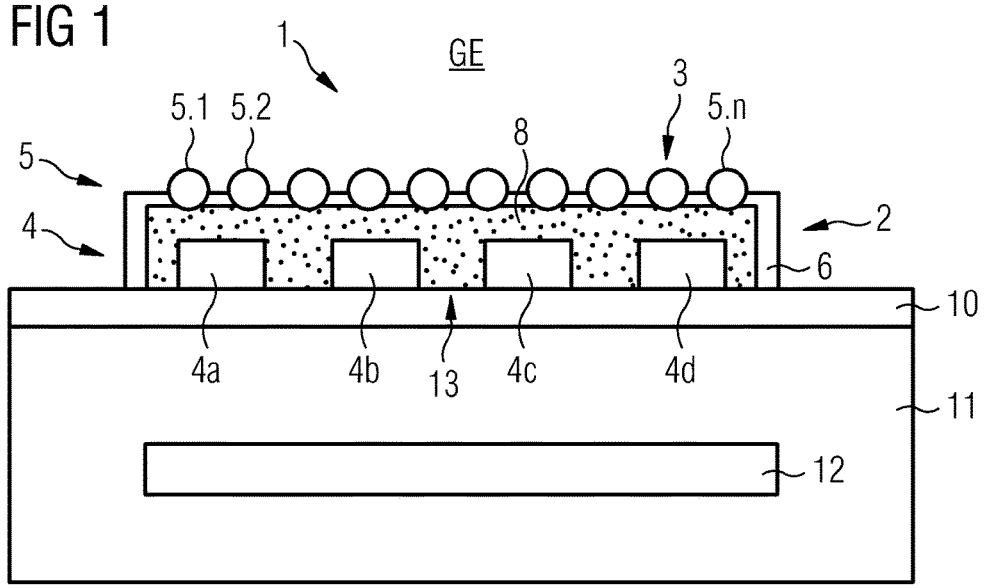
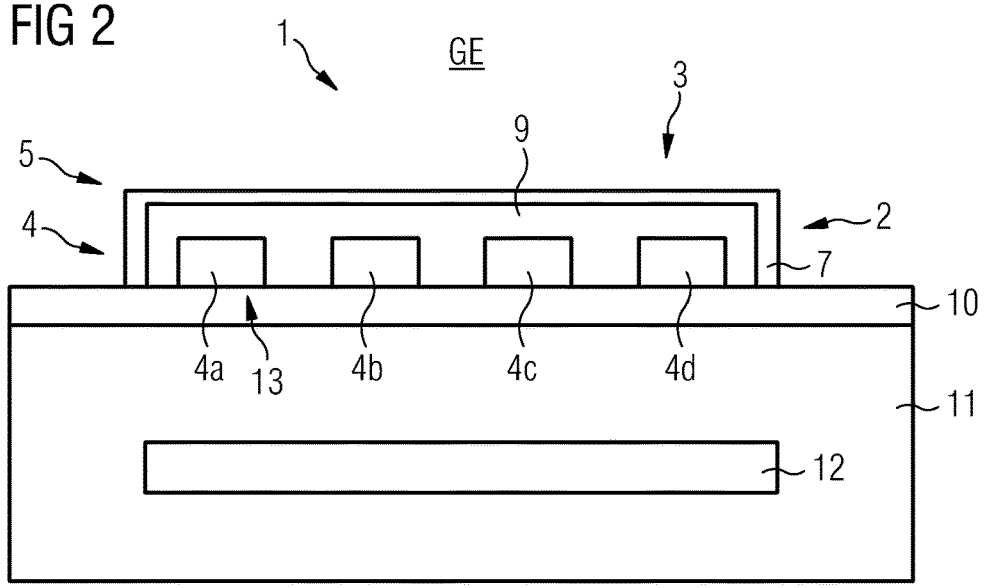

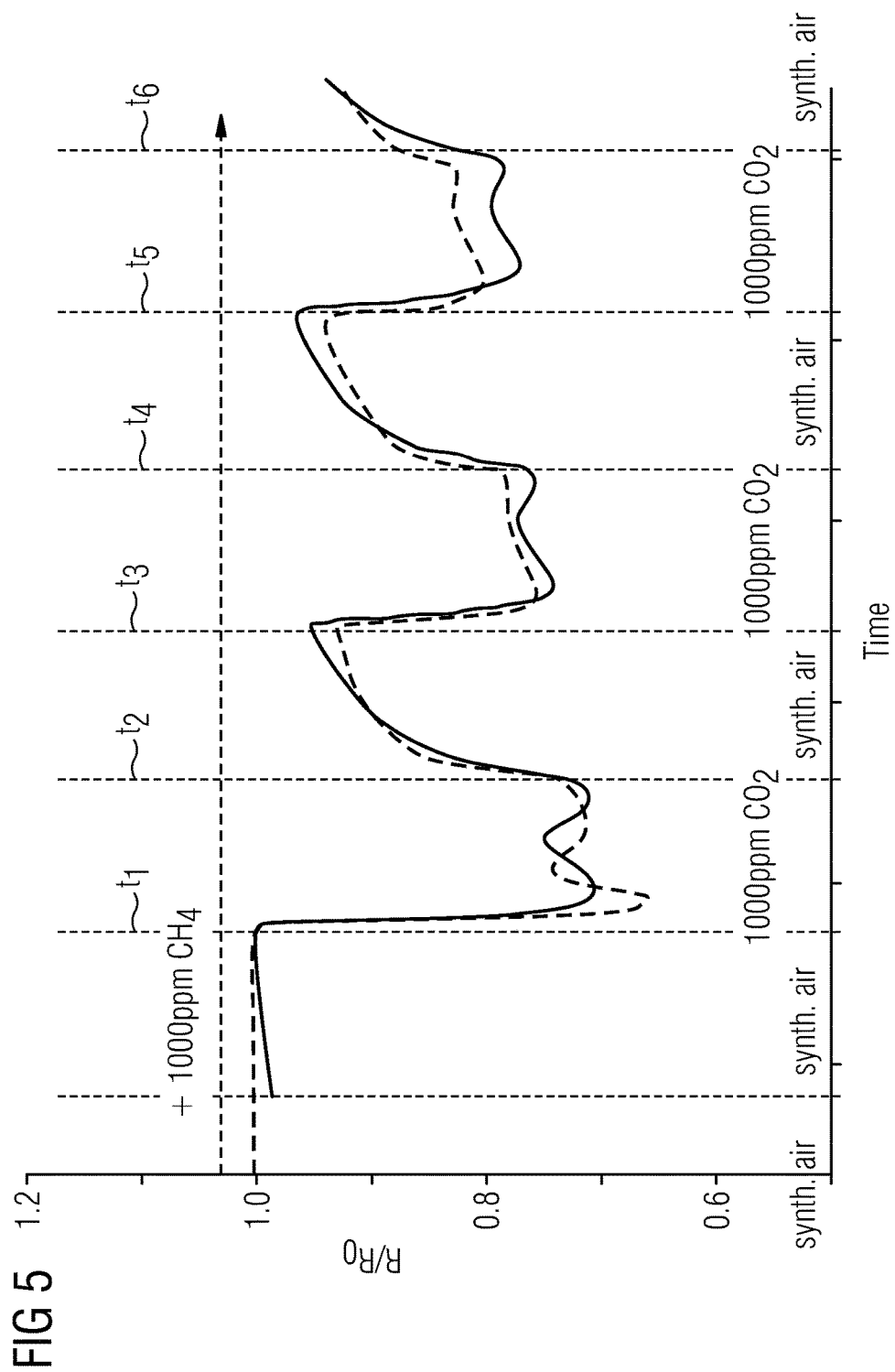

GRAPHENE GAS SENSOR FOR MEASURING THE CONCENTRATION OF CARBON DIOXIDE IN GAS ENVIRONMENTS

CROSS-REFERENCE TO RELATED APPLICATIONS

This application claims priority to German Patent Application no. 102014212282.1, filed on Jun. 26, 2014, which is incorporated herein by reference in its entirety.

FIELD

Embodiments of the disclosure relate to a gas sensor for measuring the concentration of carbon dioxide in gas environments.

BACKGROUND

Gas sensors specific to carbon dioxide ($CO_2$) gas are operated, according to the prior art, mainly in accordance with the following principles:

Infrared absorption: the sensor is specific, highly sensitive and long-term stable, but expensive (>60 USD).

Electrochemical sensors: the sensor is specific and has medium sensitivity, but exhibits low long-term stability, and the cost is somewhat lower than that of IR sensors.

Thermal conductivity: the sensors are not very specific and are insensitive, but are long-term stable and relatively low in cost.

Therefore, in general, what is needed is a sensor which meets all of the criteria of specificity, sensitivity, long-term stability, and low cost. Such a $CO_2$ sensor at a price of less than 10 USD would open up new market segments, e.g. control of air conditioning systems in buildings and automobiles.

SUMMARY

One aspect the disclosure provides a gas sensor configured to measure a concentration of carbon dioxide in a gas environment. The gas sensor comprises a graphene layer having a side facing towards the gas environment, an electrode layer comprising a plurality of electrodes electrically connected to the graphene layer, and a chalcogenide layer covering at least a part of the side facing towards the gas environment of the graphene layer.

The functional principle will be set forth as follows:

Of all materials known, graphene has the largest specific surface area (2630 m$^2$/g) and changes its electrical conductivity as a function of adsorbed gas molecules. Since graphene is a p semiconductor under ambient conditions, the adsorption of electron donators (e.g. $NH_3$) reduces its conductivity, the adsorption of electron acceptors (e.g. $NO_2$) increases its conductivity. The amount of the change in conductivity correlates with the concentration of gas molecules and returns to the initial value once the gas molecules desorb. This change in conductivity may be measured by means of a four (4) electrodes structure. [J. D. Fowler et al., Practical Chemical Sensors from Chemically Derived Graphene, ACS Nano, 3 (2009) 301; J. T. Robinson et al., Reduced Graphene Oxide Molecular Sensors, Nano Lett. 8 (2008) 3137; W. Yuan et al., Graphene-based gas sensors, J. Mater. Chem. A 1 (2013) 10078]. If the sheet resistance is significantly higher than the contact resistance toward the electrodes, it is also possible to use a two (2) electrodes configuration.

The disclosure uses graphene, functionalized with chalcogenide, as the active sensor material. Chalcogenide is a chemical compound comprising at least one chalcogen anion and at least one more electropositive element. The term chalcogenide refers in particular to sulfides, selenides, tellurides, and to oxides.

The functionalization improves adsorption of the desired types of gas, namely carbon dioxide, e.g. by chemically selective bonds, as well as possibly the extent of the charge transfer. Surprisingly it has been found that a class of materials that can be advantageously used for binding $CO_2$ is the class of chalcogenides.

The graphene layer may comprise a monolayer or multilayer graphene. The graphene itself may be undoped or doped (e.g. with nitrogen, boron, sulphur).

The chalcogenides may contain several metals and/or chalcogens; in addition, doping with foreign atoms is also possible. If there is an oxide exhibiting the highest level of metal oxidization, the sensor may readily be regenerated by heating in air in the event of degradation or contamination.

The electrodes may comprise one or more of the following electrically conductive materials: gold (Au), nickel (Ni), titanium (Ti), copper (Cu) or other metals, graphite, silicon (Si), doped silicon carbide (SiC), etc.

The disclosure provides a gas sensor that can be used in practice, as several disadvantages of the functional principle described may be overcome, namely the lack of selectivity, i.e. the inability to adsorb only carbon dioxide, and the lack of sensitivity to carbon dioxide, i.e. the inability to adsorb carbon dioxide to a sufficient extent and/or to produce a sufficient charge transfer.

Furthermore, it has to be noted that even though $CO_2$ binds to graphene surfaces, its desorption, however, is poor, which does not result in a reversible sensor response. Interference gases such as water vapor ($H_2O$) or nitrogen dioxide ($NO_2$), for example, have better binding and desorbing performances. However, these problems may be overcome by the use of a chalcogenide layer as adsorption of undesired types of gas may be suppressed.

The advantages of the sensor that has been described are manifold; for example, its manufacturing cost is very low because of its simple structure and the inexpensive raw materials. Since graphene is a carbon modification, it is chemically highly resistant, i.e. the sensor is chemically robust and age-resistant. Since graphene exhibits a large surface area, the sensor is very sensitive (possibly <ppm). Due to the manifold functionalization possibilities, a high level of selectivity may be achieved. Generally, the sensor exhibits a fast response characteristic within the range of seconds.

By means of the disclosure, the concentrations of $CO_2$ in various gas environments (e.g. indoor air, Li-ion battery cells, exhaust air of industrial plants, breathing air, etc.) are to be measured.

According to an embodiment of the disclosure the chalcogenide layer comprises metal chalcogenide, in particular copper(II) oxide (CuO), copper(I) oxide ($Cu_2O$), copper(II) sulfide (CuS), copper(I) sulfide ($Cu_2S$), titanium dioxide ($TiO_2$), and/or cobalt(II,III) oxide ($Co_3O_4$).

According to an embodiment of the disclosure the chalcogenide layer comprises a chalcogenide nanoparticle layer. Functionalization of the graphene layer with metal chalcogenides is effected in one embodiment with nanoparticles typically having a diameter of 1 . . . 500 nm.

Deposition of the chalcogenide nanoparticles, in particular of the metal chalcogenide nanoparticles, may take place either chemically or electrochemically. Chemical deposition may be effected by using a metal salt and a reducing agent, but may also be effected while using the metal salt as the reducing agent for the graphene oxide substrate. Chemically coating the graphene with the chalcogenide nanoparticles, in particular with the metal chalcogenide nanoparticles, is possible both in suspension and on the layer that has already been deposited.

According to an embodiment of the disclosure the gas sensor comprises a passivation layer covering parts, which are not covered by the chalcogenide layer, of the side facing towards the gas environment of the graphene layer.

The passivation layer may be manufactured by modifying the graphene surface, e.g. by means of fluorination (e.g. with $XeF_2$ or fluorine-containing plasmas) or silanization (e.g. with HMDS or $SiH_4$). The passivation layer may comprise a different material than graphene, e.g. of a fluoropolymer (e.g. Nafion). It is possible that at first, the passivation layer is deposited directly onto the graphene, followed by the nanoparticles being deposited thereon. Alternatively, it is also possible to initially deposit the nanoparticles and to deposit the passivation layer thereon (which deposition will be at least partially planarizing). Subsequently, the nanoparticles are re-exposed by means of back-etching (e.g., in the case of a polymer layer, by using an oxygen plasma).

The passivation layer may also be selectively deposited onto the graphene layer on the parts not covered by the chalcogenide layer, e.g. by means of chemical modification of the graphene itself.

By these features it may be avoided that interference gases are binding to such parts of the side facing towards the gas environment of the graphene layer, which are not covered by the chalcogenide layer, for example parts, which are exposed between the nanoparticles of the chalcogenide layer.

According to an embodiment of the disclosure the passivation layer is impermeable to an interference gas, such as $H_2O$, $NO_2$, $H_2S$, of the gas environment.

For example, the passivation layer may comprise chemically modified graphene, in particular graphene oxide, reduced graphene oxide, fluorographene, silanized graphene and/or graphane.

According to an embodiment of the disclosure the passivation layer is hydrophobic. In this way absorption of water vapor on the graphene layer may be avoided.

According to an embodiment of the disclosure the passivation layer comprises chemically modified graphene, in particular reduced graphene oxide, fluorographene, silanized graphene and/or graphane. Such materials are hydrophobic so that absorption of water vapor on the graphene layer may be avoided. For the purpose of fluorination xenon difluoride ($XeF_2$) or fluorine-containing plasmas and for the purpose of silanization hexamethyldisilazane (HMDS) or silane ($SiH_4$) may be used.

According to an embodiment of the disclosure the passivation layer comprises a hydrophobic polymer, in particular a fluoropolymer. By these features absorption of water vapor on the graphene layer may be avoided in an easy way.

According to an embodiment of the disclosure the passivation layer is selectively gas-permeable for carbon dioxide. If the passivation layer comprises a selectively gas-permeable material back-etching may be dispensed with, and selectivity may be at least partially achieved by the filtering effect of the passivation layer. By these features the selectivity of the gas sensor may be increased.

According to an embodiment of the disclosure the graphene layer comprises chemically modified graphene, in particular reduced graphene oxide, fluorographene, silanized graphene and/or graphane.

This chemical modification may serve as a passivation against interference gases. By these features the graphene layer itself shows a hydrophobic behavior so that absorption of water vapor on the graphene layer may be avoided without the need for a separate passivation layer.

According to an embodiment of the disclosure the chalcogenide layer comprises a continuous chalcogenide layer. The continuous layer may have a typical thickness of 10 . . . 500 nm. In that case, the passivation layer may be dispensed with.

According to an embodiment of the disclosure the graphene layer comprises a graphene floc layer. The graphene layer may comprise mutually contacting graphene flocs forming a graphene floc layer. The graphene flocs may be deposited by spinning, dripping or spraying a graphene suspension onto the electrode structure. What is also possible is to deposit a graphene oxide suspension, followed by chemical, thermal, photochemical or plasma-chemical reduction to yield graphene.

According to an embodiment of the disclosure the graphene layer comprises a continuous graphene layer. The graphene layer may comprise a continuous graphene film. The continuous graphene layer may be produced by means of exfoliation from a graphite crystal, by epitaxial deposition onto silicon carbide (SiC), by means of chemical vapor deposition (CVD) and subsequent transfer or by segregation from solid-state sources.

According to an embodiment of the disclosure the graphene layer, the electrode layer and the chalcogenide layer are arranged on an insulator layer and a substrate layer, wherein the insulator layer is arranged in such way that the graphene layer, the electrode layer and/or the chalcogenide layer are electrically isolated from the substrate layer. The substrate may comprise silicon (Si), whereas the insulator layer may comprise the following materials: silicon dioxide ($SiO_2$), glass, various polymers (e.g. polyimide), silicon carbide (SiC).

According to an embodiment of the disclosure the substrate layer comprises an electrical heating element. In principle, the sensor may be operated at room temperature and, therefore, heating may be dispensed with. If heating is nevertheless required, in specific embodiments, e.g. for regeneration purposes or in order to increase selectivity toward $H_2O$, only small heating power will be required because of the small amount of sensor mass and the low temperature required, namely from 80 to 150° C. The substrate may be provided with a heater, which may increase regeneration and insensitivity toward adsorption of interference gases (e.g. $H_2O$). Heating may also be realized by means of current conduction through the graphene layer itself.

According to an embodiment of the disclosure the electrodes are arranged on a side of the graphene layer facing away from the gas environment. The electrodes may in principle contact the graphene layer from below, from above or from the side. However in one embodiment the electrodes contact the graphene layer from below. By these features the sensitive surface of the gas sensor and thereby the sensitivity of the gas sensor may be increased.

In a further aspect the disclosure provides a method for manufacturing a gas sensor for measuring a concentration of carbon dioxide in a gas environment, the method comprises providing a graphene layer having a side facing towards the gas environment, providing an electrode layer comprising a plurality of electrodes electrically connected to the graphene layer, and providing a chalcogenide layer covering at least a part of the side facing towards the gas environment of the graphene layer.

BRIEF DESCRIPTION OF THE DRAWINGS

Embodiments of the present disclosure are described herein making reference to the appended drawings.

FIG. 1 shows a schematic side view of a first embodiment of a gas sensor according to the disclosure;

FIG. 2 shows a schematic side view of a second embodiment of a gas sensor according to the disclosure;

FIG. 5 illustrates further examples of the response of a gas sensor according to the disclosure to changes of the concentration of carbon dioxide in the gas environment over time.

Figure 3:
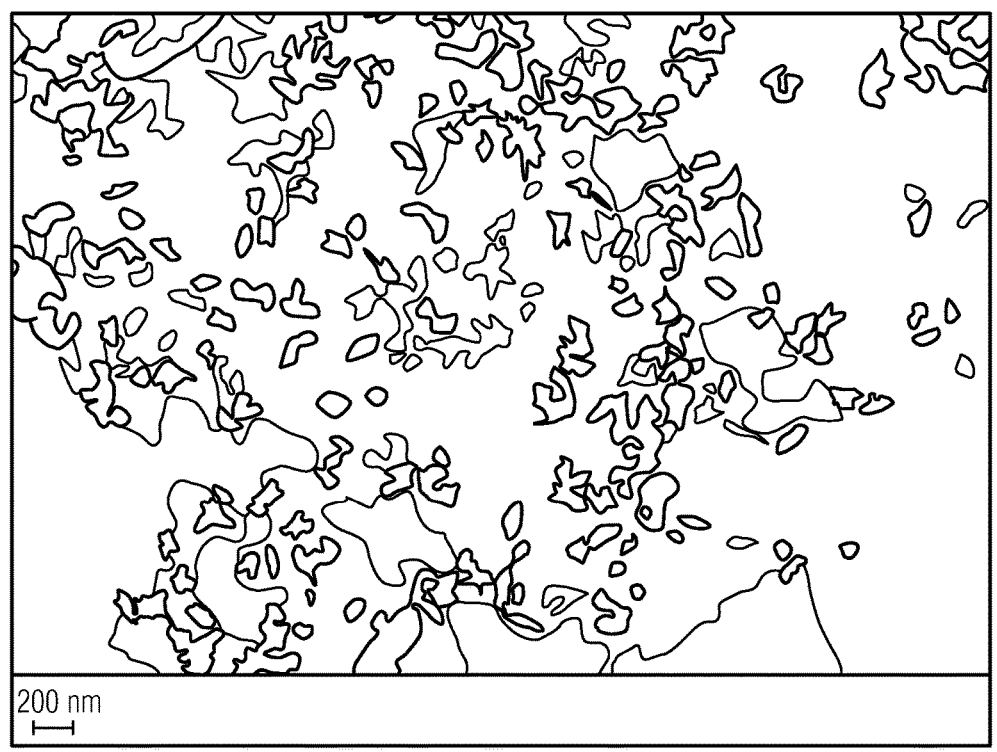
FIG. 3 shows a micrograph of a part of a third embodiment of a gas sensor according to the disclosure.

Equal or equivalent elements or elements with equal or equivalent functionality are denoted in the following description by equal or equivalent reference numerals.

DETAILED DESCRIPTION

In the following description, a plurality of details is set forth to provide a more thorough explanation of embodiments of the present disclosure. However, it will be apparent to those skilled in the art that embodiments of the present disclosure may be practiced without these specific details. In other instances, well-known structures and devices are shown in block diagram form rather than in detail in order to avoid obscuring embodiments of the present disclosure. In addition, features of the different embodiments described hereinafter may be combined with each other, unless specifically noted otherwise.

FIG. 1 shows a schematic side view of a first embodiment of a gas sensor 1 according to the disclosure.

In one aspect the disclosure provides a gas sensor 1 for measuring a concentration of carbon dioxide in a gas environment GE. The gas sensor 1 comprises a graphene layer 2 having a side 3 facing towards the gas environment GE, an electrode layer for comprising a plurality of electrodes 4a-d electrically connected to the graphene layer 2, and a chalcogenide layer 5 covering at least a part of the side 3 facing towards the gas environment GE of the graphene layer 2.

The functional principle will be set forth as follows:

Of all materials known, graphene has the largest specific surface area (2630 $m^2/g$) and changes its conductivity as a function of adsorbed gas molecules. Since graphene is a p semiconductor under ambient conditions, the adsorption of electron donators (e.g. $NH_3$) reduces its conductivity, the adsorption of electron acceptors (e.g. $NO_2$) increases its conductivity. The amount of the change in conductivity correlates with the concentration of gas molecules and returns to the initial value once the gas molecules desorb. This change in conductivity may be measured by means of a 4 electrodes structure. [See J. D. Fowler et al., Practical Chemical Sensors from Chemically Derived Graphene, ACS Nano, 3 (2009) 301; J. T. Robinson et al., Reduced Graphene Oxide Molecular Sensors, Nano Lett. 8 (2008) 3137; W. Yuan et al., Graphene-based gas sensors, J. Mater. Chem. A 1 (2013) 10078], which is hereby incorporated by reference.

If the sheet resistance is significantly higher than the contact resistance toward the electrodes, it is also possible to use a 2 electrodes configuration.

The disclosure uses graphene, functionalized with chalcogenide, as the active sensor material. Chalcogenide is a chemical compound comprising at least one chalcogen anion and at least one more electropositive element. The term chalcogenide refers in particular to sulfides, selenides, tellurides, and to oxides.

The functionalization improves adsorption of the desired types of gas, namely carbon dioxide, e.g. by chemically selective bonds, as well as possibly the extent of the charge transfer. Surprisingly it has been found that a class of materials that can be advantageously used for binding $CO_2$ is the class of chalcogenides.

The graphene layer 2 may comprise a monolayer or multilayer graphene. The graphene itself may be undoped or doped (e.g. with nitrogen, boron, sulphur).

The chalcogenides may contain several metals and/or chalcogens; in addition, doping with foreign atoms is also possible. If there is an oxide exhibiting the highest level of metal oxidization, the sensor may readily be regenerated by heating in air in the event of degradation or contamination.

The electrodes 4a-4d may comprise the following electrically conductive materials: gold (Au), nickel (Ni), titanium (Ti), copper (Cu) or other metals, graphite, silicone (Si), doped silicon carbide (SiC), etc.

The disclosure provides a gas sensor 1 that can be used in practice, as several disadvantages of the functional principle described may be overcome, namely the lack of selectivity, i.e. the inability to adsorb only carbon dioxide, and the lack of sensitivity to carbon dioxide, i.e. the inability to adsorb carbon dioxide to a sufficient extent and/or to produce a sufficient charge transfer.

Furthermore, it has to be noted that even though $CO_2$ binds to graphene surfaces, its desorption, however, is poor, which does not result in a reversible sensor response. Interference gases such as water vapor ($H_2O$) or nitrogen dioxide ($NO_2$), for example, have better binding and desorbing performances. However, these problems may be overcome by the use of a chalcogenide layer as adsorption of undesired types of gas may be suppressed.

The advantages of the gas sensor 1 that has been described are manifold; for example, its manufacturing cost is very low because of its simple structure and the inexpensive raw materials. Since graphene is a carbon modification, it is chemically highly resistant, i.e. the gas sensor 1 is chemically robust and age-resistant. Since graphene exhibits a large surface area, the sensor 1 is very sensitive (possibly <ppm). Due to the manifold functionalization possibilities, a high level of selectivity may be achieved. Generally, the sensor 1 exhibits a fast response characteristic within the range of seconds.

By means of the disclosure, the concentrations of $CO_2$ in various gas environments (e.g. indoor air, Li-ion battery cells, exhaust air of industrial plants, breathing air, etc.) may be measured.

According to an embodiment of the disclosure the chalcogenide layer 5 comprises metal chalcogenide, in particular copper(II) oxide (CuO), copper(I) oxide ($Cu_2O$), copper(II) sulfide (CuS), copper(I) sulfide ($Cu_2S$), titanium dioxide ($TiO_2$), and/or cobalt(II,III) oxide ($Co_3O_4$).

According to an embodiment of the disclosure the chalcogenide layer comprises a chalcogenide nanoparticle layer. Functionalization of the graphene layer 5 with metal chalcogenides is effected for example with nanoparticles 5.1-$n$ typically having a diameter of 1 . . . 500 nm.

Deposition of the chalcogenide nanoparticles 5.1-$n$, in particular of the metal chalcogenide nanoparticles 5.1-$n$, may take place either chemically or electrochemically. Chemical deposition may be effected by using a metal salt and a reducing agent, but may also be effected while using the metal salt as the reducing agent for the graphene oxide substrate. Chemically coating the graphene with the chalcogenide nanoparticles 5.1-$n$, in particular with the metal chalcogenide nanoparticles 5.1-$n$, is possible both in suspension and on the layer that has already been deposited.

According to an embodiment of the disclosure the gas sensor 1 comprises a passivation layer 6 covering parts, which are not covered by the chalcogenide layer 5, of the side 3 facing towards the gas environment GE of the graphene layer 2.

The passivation layer 6 may be manufactured by modifying the graphene surface, e.g. by means of fluorination (e.g. with $XeF_2$ or fluorine-containing plasmas) or silanization (e.g. with HMDS or $SiH_4$). The passivation layer 6 may comprise a different material than graphene, e.g. of a fluoropolymer (e.g. Nafion). It is possible that at first, the passivation layer 6 is deposited directly onto the graphene, followed by the nanoparticles 5.1-$n$ being deposited thereon. Alternatively, it is also possible to initially deposit the nanoparticles and to deposit the passivation layer 6 thereon (which deposition will be at least partially planarizing). Subsequently, the nanoparticles 5.1-$n$ are re-exposed by means of back-etching (e.g., in the case of a polymer layer 6, by using an oxygen plasma).

The passivation layer 6 may also be selectively deposited onto the graphene layer 2 on the parts not covered by the chalcogenide layer 5, e.g. by means of chemical modification of the graphene itself.

By these features it may be avoided that interference gases are binding to such parts of the side 3 facing towards the gas environment GE of the graphene layer, which are not covered by the chalcogenide layer 5, for example parts, which are exposed between the nanoparticles 5.1-$n$ of the chalcogenide layer 5.

According to an embodiment of the disclosure the passivation layer 6 is hydrophobic. In this way absorption of water vapor on the graphene layer 2 may be avoided.

According to an embodiment of the disclosure the passivation layer 6 comprises chemically modified graphene, in particular, reduced graphene oxide, fluorographene, silanized graphene and/or graphane. Such materials are hydrophobic so that absorption of water vapor on the graphene layer may be avoided. For the purpose of fluorination xenon difluoride ($XeF_2$) or fluorine-containing plasmas and for the purpose of silanization hexamethyldisilazane (HMDS) or silane ($SiH_4$) may be used.

According to an embodiment of the disclosure the passivation layer 6 comprises a hydrophobic polymer, in particular a fluoropolymer. By these features absorption of water vapor on the graphene layer may be avoided in an easy way.

According to an embodiment of the disclosure the passivation layer 6 is selectively gas-permeable for carbon dioxide. If the passivation layer 6 comprises a selectively gas-permeable material back-etching may be dispensed with, and selectivity may be at least partially achieved by the filtering effect of the passivation layer 6. By these features the selectivity of the gas sensor 1 may be increased.

According to an embodiment of the disclosure the graphene layer 2 comprises chemically modified graphene, in particular reduced graphene oxide, fluorographene, silanized graphene and/or graphane.

This chemical modification may serve as a passivation against interference gases. By these features the graphene layer 2 itself shows a hydrophobic behavior so that absorption of water vapor on the graphene layer 2 may be avoided without the need for a separate passivation layer 6.

According to an embodiment of the disclosure the graphene layer 2 comprises a graphene floc layer 8. The graphene layer 2 may comprise mutually contacting graphene flocs forming a graphene floc layer 8. The graphene flocs may be deposited by spinning, dripping or spraying a graphene suspension onto the electrode structure. What is also possible is to deposit a graphene oxide suspension, followed by chemical, thermal, photochemical or plasma-chemical reduction to yield graphene.

According to an embodiment of the disclosure the graphene layer 2, the electrode layer for and the chalcogenide layer 5 are arranged on an insulator layer 10 and a substrate layer 11, wherein the insulator layer 10 is arranged in such way that the graphene layer 2, the electrode layer for and/or the chalcogenide layer 5 are electrically isolated from the substrate layer 11. The substrate 11 may comprise silicon (Si), whereas the insulator layer 10 may comprise the following materials: silicon dioxide ($SiO_2$), glass, various polymers (e.g. polyimide), silicon carbide (SiC).

According to an embodiment of the disclosure the substrate layer 11 comprises an electrical heating element 12. In principle, the sensor 1 may be operated at room temperature and, therefore, heating may be dispensed with. If heating is nevertheless required, in specific embodiments, e.g. for regeneration purposes or in order to increase selectivity toward $H_2O$, only small heating power will be required because of the small amount of sensor mass and the low temperature required, namely from 80 to 150° C. The substrate 11 may be provided with a heater 12, which may increase regeneration and insensitivity toward adsorption of interference gases (e.g. $H_2O$). Heating may also be realized by means of current conduction through the graphene layer 2 itself.

According to an embodiment of the disclosure the electrodes 4a-4d are arranged on a side 13 of the graphene layer 2 facing away from the gas environment GE. The electrodes 4a-4d may in principle contact the graphene layer 2 from below, from above or from the side. However it is preferred that the electrodes 4a-4d contact the graphene layer 2 from below. By these features the sensitive surface of the gas sensor 1 and thereby the sensitivity of the gas sensor 1 may be increased.

In a further aspect the disclosure provides a method for manufacturing a gas sensor 1 for measuring a concentration of carbon dioxide in a gas environment GE, the method comprises providing a graphene layer 2 having a side 3 facing towards the gas environment GE, providing an electrode layer 4 comprising a plurality of electrodes 4a-4d electrically connected to the graphene layer 2, and providing a chalcogenide layer 5 covering at least a part of the side 3 facing towards the gas environment GE of the graphene layer 2.

FIG. 2 shows a schematic side view of a second embodiment of a gas sensor 1 according to the disclosure.

The second embodiment of the gas sensor 1 is based on the first embodiment of the gas sensor 1. In the following, only the differences between the embodiments discussed.

According to an embodiment of the disclosure the chalcogenide layer 5 comprises a continuous chalcogenide layer 7. The continuous layer may have a typical thickness of 10 . . . 500 nm. In that case, the passivation layer may be dispensed with.

According to an embodiment of the disclosure the graphene layer 2 comprises a continuous graphene layer 9. The graphene layer 2 may comprise a continuous graphene film 9. The continuous graphene layer 9 may be produced by means of exfoliation from a graphite crystal, by epitaxial deposition onto silicon carbide (SiC), by means of chemical vapor deposition (CVD) and subsequent transfer or by segregation from solid-state sources.

Naturally, the graphene layer 2 may also comprise a graphene floc layer.

FIG. 3 shows a micrograph of a part of a third embodiment of a gas sensor according to the disclosure. This embodiment comprises for example a graphene layer 2 which is partly covered by copper oxide nano particles forming the chalcogenide layer 5. The plane areas shown in FIG. 3 are parts of the graphene layer 2, which are not covered by the chalcogenide layer 5, on the side 3 facing towards the gas environment GE of the graphene layer 2. The elevated portions shown in FIG. 3 are the copper oxide nano particles forming the chalcogenide layer 5.

Figure 4:
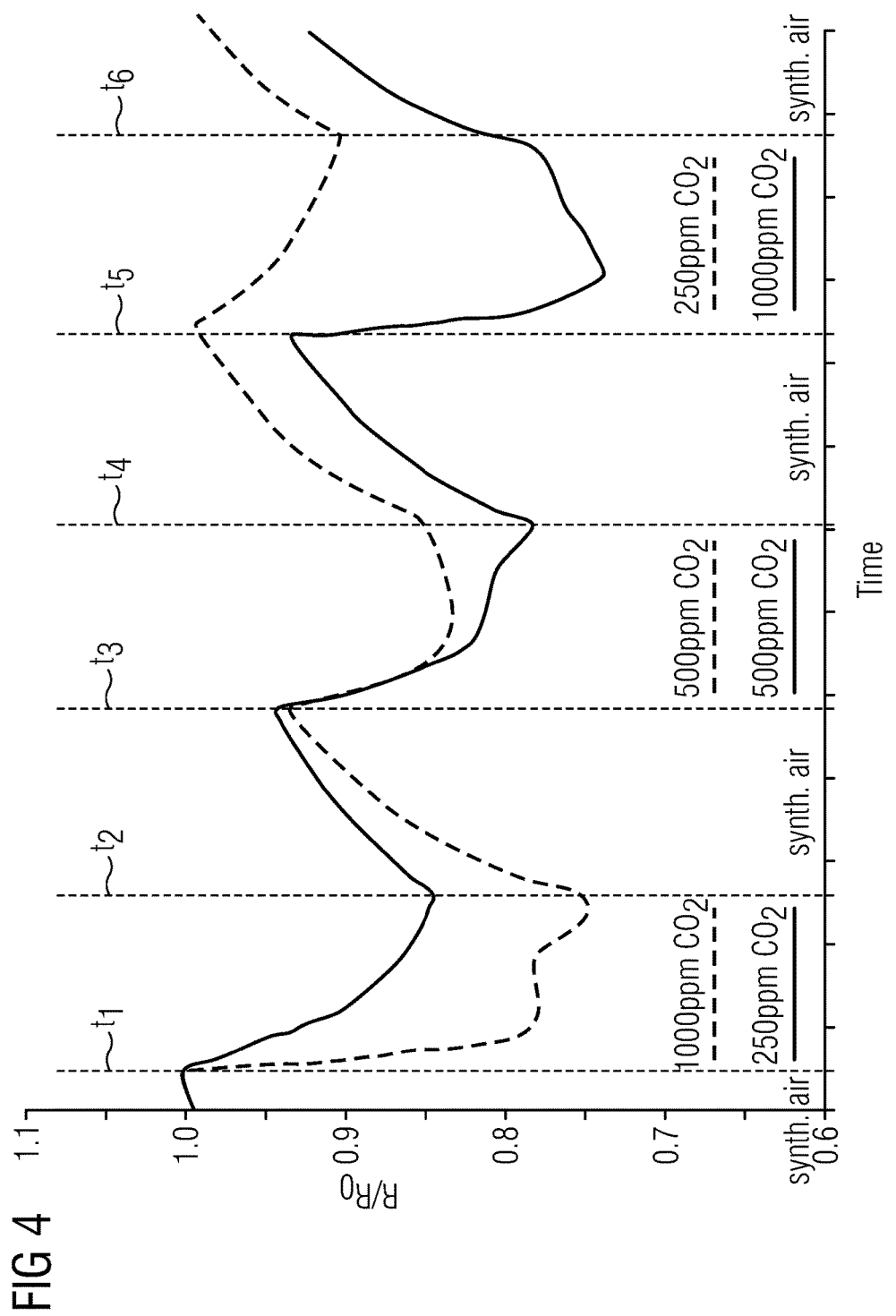
FIG. 4 illustrates examples of the response of a gas sensor according to the disclosure to changes of the concentration of carbon dioxide in the gas environment over time.

FIG. 4 illustrates two examples of the response of a gas sensor 1 according to the disclosure to changes of the concentration of carbon dioxide in the gas environment GE over time.

In a first example the concentration of carbon dioxide rises at time t1 from 0 ppm to 1000 ppm. At time t2 the concentration falls back to 0 ppm. Furthermore, at time t3 the concentration reaches 500 ppm and a time t4 is set again to 0 ppm. At time t5 it rises to 250 ppm and finally drops to 0 ppm at time t6. The response of the sensor 1 is shown as a dashed line depicting a relative change of the resistance of the graphene layer.

In a second example the concentration of carbon dioxide rises at time t1 from 0 ppm to 250 ppm. At time t2 the concentration falls back to 0 ppm. Furthermore, at time t3 the concentration reaches 500 ppm and at time t4 is set again to 0 ppm. At time t5 it rises to 1000 ppm and finally drops to 0 ppm at time t6. The response of the sensor 1 is shown as a solid line depicting a relative change of the resistance of the graphene layer.

FIG. 5 illustrates further examples of the response of a gas sensor 1 according to the disclosure to changes of the concentration of carbon dioxide in the gas environment over time.

In a first example the concentration of carbon dioxide rises at time t1 from 0 ppm to 1000 ppm. At time t2 the concentration falls back to 0 ppm. Furthermore, at time t3 the concentration reaches 1000 ppm and at time t4 is set again to 0 ppm. At time t5 it rises to 1000 ppm and finally drops to 0 ppm at time t6. The response of the sensor 1 is shown as a solid line depicting a relative change of the resistance of the graphene layer. In the first example of FIG. 5 it is assumed that no interference gases are present.

In contrast of that in a second example of FIG. 5 it is assumed that there is a presence of methane $CH_4$ having a concentration of 1000 ppm. The response of the sensor 1 is shown as a dashed line depicting a relative change of the resistance of the graphene layer.

The disclosure may be summarized as follows: The core of the disclosure is a $CO_2$ gas sensor based on graphene functionalized with metal chalcogenide in combination with passivation of the non-functionalized graphene surfaces.

The disclosure may be embodied in different forms.

The substrate may comprise the following materials: Si with $SiO_2$ or a different electrically insulating layer, glass, polymer (e.g. polyimide), SiC. Additionally, the substrate may be provided with a heater, which may increase regeneration and insensitivity toward adsorption of interference gases (e.g. $H_2O$). Heating may also be realized by means of current conduction through the graphene layer itself.

The electrodes may comprise the following electrically conductive materials: Au, Ni, Ti, Cu or other metals, graphite, Si, doped SiC, etc. The electrodes may contact the graphene layer from below (which is preferred), from above or from the side.

The graphene layer may comprise a continuous graphene film or of mutually contacting graphene floc. The continuous graphene layer may be produced by means of exfoliation from a graphite crystal, by epitaxial deposition onto SiC, by means of CVD and subsequent transfer or by segregation from solid-state sources. The graphene floc may also be deposited by spinning, dripping or spraying a graphene suspension onto the electrode structure. What is also possible is to deposit a graphene oxide suspension, followed by chemical, thermal, photochemical or plasma-chemical reduction to yield graphene. The graphene layer may comprise a monolayer or multilayer graphene. The graphene itself may be undoped, doped (e.g. with nitrogen, boron, sulphur), and be chemically modified (e.g. reduced graphene oxide, fluorographene, graphane, etc.). This chemical modification may serve as a passivation against interference gases. It is possible for the entire graphene layer to be modified or for a modified graphene layer to be deposited on an unmodified graphene layer. Likewise, it is possible that only the graphene surface is modified, e.g. by means of fluorination (e.g. with $XeF_2$ or fluorine-containing plasmas) or silanization (e.g. with HMDS or $SiH_4$). The passivation layer may comprise a different material than graphene, e.g. of a fluoropolymer (e.g. Nafion). It is possible that at first, the passivation layer is deposited directly onto the graphene, followed by the nanoparticles being deposited thereon. Alternatively, it is also possible to initially deposit the nanoparticles and to deposit the passivation layer thereon (which deposition will be at least partially planarizing). Subsequently, the nanoparticles are re-exposed by means of back-etching (e.g., in the case of a polymer layer, by using an oxygen plasma). This top coating may also comprise a selectively gas-permeable material. In this case, back-etching is dispensed with, and selectivity is at least partially achieved by the filtering effect of the top coating. The passivation layer may also be selectively deposited onto the graphene between the nanoparticles, e.g. by means of chemical modification of the graphene itself (see below).

Functionalization of the graphene layer with metal chalcogenides (e.g. $CuO$, $Cu_2O$, $CuS$, $Cu_2S$, $TiO_2$, $Co_3O_4$) is effected in one embodiment with nanoparticles (typical diameter of 1 . . . 500 nm). However, it is also possible with a continuous layer (typical thickness of 10 . . . 500 nm). In the latter case, the passivation layer is dispensed with. The metal chalcogenides may contain several metals and/or chalcogens; in addition, doping with foreign atoms is also possible. If there is an oxide exhibiting the highest level of metal oxidization, the sensor may readily be regenerated by heating in air in the event of degradation or contamination. Deposition of the metal chalcogenide nanoparticles may take place either chemically or electrochemically. Chemical deposition may be effected by using a metal salt and a reducing agent, but may also be effected while using the metal salt as the reducing agent for the graphene oxide substrate. Chemically coating the graphene with the metal chalcogenide nanoparticles is possible both in suspension and on the layer that has already been deposited.

An embodiment of the sensor is based on the combination of thermally reduced graphene oxide, CuO nanoparticles which have been electrochemically deposited thereon and a fluorinated polymer as the passivation layer.

The above described is merely illustrative, and it is understood that modifications and variations of the arrangements and the details described herein will be apparent to others skilled in the art. It is the intent, therefore, to be limited only by the scope of the impending claims and not by the specific details presented by way of description and explanation above.

What is claimed is:

1. A gas sensor for measuring a concentration of carbon dioxide in a gas environment (GE), the gas sensor comprising:
   a graphene layer having a first side facing towards the gas environment (GE);
   an electrode layer comprising a plurality of electrode electrically connected to the graphene layer;
   a chalcogenide layer covering a part of the first side of the graphene layer facing towards the gas environment (GE); and
   a passivation layer, which is a different material than the graphene layer, wherein the passivation layer is selectively disposed directly on the first side of the graphene layer that is not covered by but in direct contact with the chalcogenide layer; wherein the chalcogenide layer is deposited before the passivation layer and the chalcogenide layer is exposed to the GE.

2. A gas sensor according to claim 1, wherein the chalcogenide layer comprises a metal chalcogenide.

3. A gas sensor according to claim 1, wherein the chalcogenide layer comprises a chalcogenide nanoparticle layer.

4. A gas sensor according to claim 1, wherein the passivation layer is impermeable to an interference gas of the gas environment.

5. A gas sensor according to claim 1, wherein the passivation layer comprises chemically modified graphene.

6. A gas sensor according to claim 1, wherein the passivation layer comprises a hydrophobic polymer.

7. A gas sensor according to claim 1, wherein the passivation layer is selectively gas-permeable for carbon dioxide.

8. A gas sensor according to claim 1, wherein the graphene layer comprises chemically modified graphene.

9. A gas sensor according to claim 1, wherein the graphene layer comprises a graphene floc layer.

10. A gas sensor according to claim 1, wherein the graphene layer comprises a continuous graphene layer.

11. A gas sensor according to claim 1, wherein the graphene layer, the electrode layer and the chalcogenide layer are arranged on an insulator layer and a substrate layer, wherein the insulator layer is arranged in such way that the graphene layer, the electrode layer and/or the chalcogenide layer are electrically isolated from the substrate layer.

12. A gas sensor according to claim 11, wherein the substrate layer comprises an electrical heating element embedded within the substrate.

13. A gas sensor according to claim 1, wherein the electrodes are arranged on a second side of the graphene layer, opposite the first side of the graphene layer facing away from the gas environment (GE).

14. A method for manufacturing a gas sensor for measuring a concentration of carbon dioxide in a gas environment (GE), the method comprising:
   providing a graphene layer having a first side facing towards the gas environment (GE);
   providing an electrode layer comprising a plurality of electrodes electrically connected to the graphene layer;
   providing a chalcogenide layer covering a part of the first side facing towards the gas environment (GE) of the graphene layer; and
   forming a passivation layer, which is a different material than the graphene layer, wherein the passivation layer is selectively disposed directly on the first side of the graphene layer that is not covered by but in direct contact with the chalcogenide layer; wherein the chalcogenide layer is deposited before the passivation layer and the chalcogenide layer is exposed to the GE.

* * * * *